(12) United States Patent
Lin et al.

(10) Patent No.: US 7,659,731 B2
(45) Date of Patent: Feb. 9, 2010

(54) LIQUID PROPERTIES SENSOR CIRCUIT

(75) Inventors: Yingjie Lin, El Paso, TX (US); Su-Chee Simon Wang, Troy, MI (US); Norberto Hernandez Resendiz, Juarez (MX)

(73) Assignee: Delphi Technologies, Inc., Troy, MI (US)

( * ) Notice: Subject to any disclaimer, the term of this patent is extended or adjusted under 35 U.S.C. 154(b) by 161 days.

(21) Appl. No.: 12/031,880

(22) Filed: Feb. 15, 2008

(65) Prior Publication Data
US 2008/0197863 A1    Aug. 21, 2008

Related U.S. Application Data

(60) Provisional application No. 60/890,112, filed on Feb. 15, 2007.

(51) Int. Cl.
*G01R 27/08* (2006.01)
*G01N 27/42* (2006.01)

(52) U.S. Cl. .................................. 324/693; 324/439

(58) Field of Classification Search ................ 324/693, 324/439, 691, 649, 600, 698, 686, 664, 663, 324/658, 634, 640, 643, 689, 694, 722, 425; 340/603, 631; 702/22, 50, 183; 73/304 R, 73/53.01, 5
See application file for complete search history.

(56) References Cited

U.S. PATENT DOCUMENTS

| 4,559,457 A | 12/1985 | Sugawara |
| 5,969,437 A | 10/1999 | Foerster |
| 6,377,052 B1 * | 4/2002 | McGinnis et al. ........... 324/446 |
| 7,043,402 B2 | 5/2006 | Phillips et al. |
| 2004/0012399 A1 | 1/2004 | Lin et al. |
| 2004/0177817 A1 * | 9/2004 | Bradenbaugh ........... 122/13.01 |
| 2007/0236469 A1 * | 10/2007 | Woolley et al. ............. 345/173 |

OTHER PUBLICATIONS

PCT Search Report dated Mar. 18, 2008.

\* cited by examiner

*Primary Examiner*—Hoai-An D Nguyen
(74) *Attorney, Agent, or Firm*—Thomas N. Twomey

(57) ABSTRACT

A sensor circuit is coupled to a sensing element for determining a property, such as a dielectric constant, of a fuel. The circuit includes an excitation voltage signal generator, a synchronization trigger and a processing circuit configured to generate an output signal indicative of the fuel property. The excitation signal is applied to the sensing element to produce an induced current signal. The synchronization trigger generates a trigger signal when the excitation signal crosses zero volts, at which time the real (resistive) component of the induced current signal is zero. The induced signal is therefore wholly representative of the imaginary component attributable to a capacitance of the fuel, which in turn is dependent on the dielectric constant (and thus ethanol concentration) of the fuel blend. The processing circuit is configured to sample the induced signal in response to the trigger signal and produce the output signal.

14 Claims, 3 Drawing Sheets

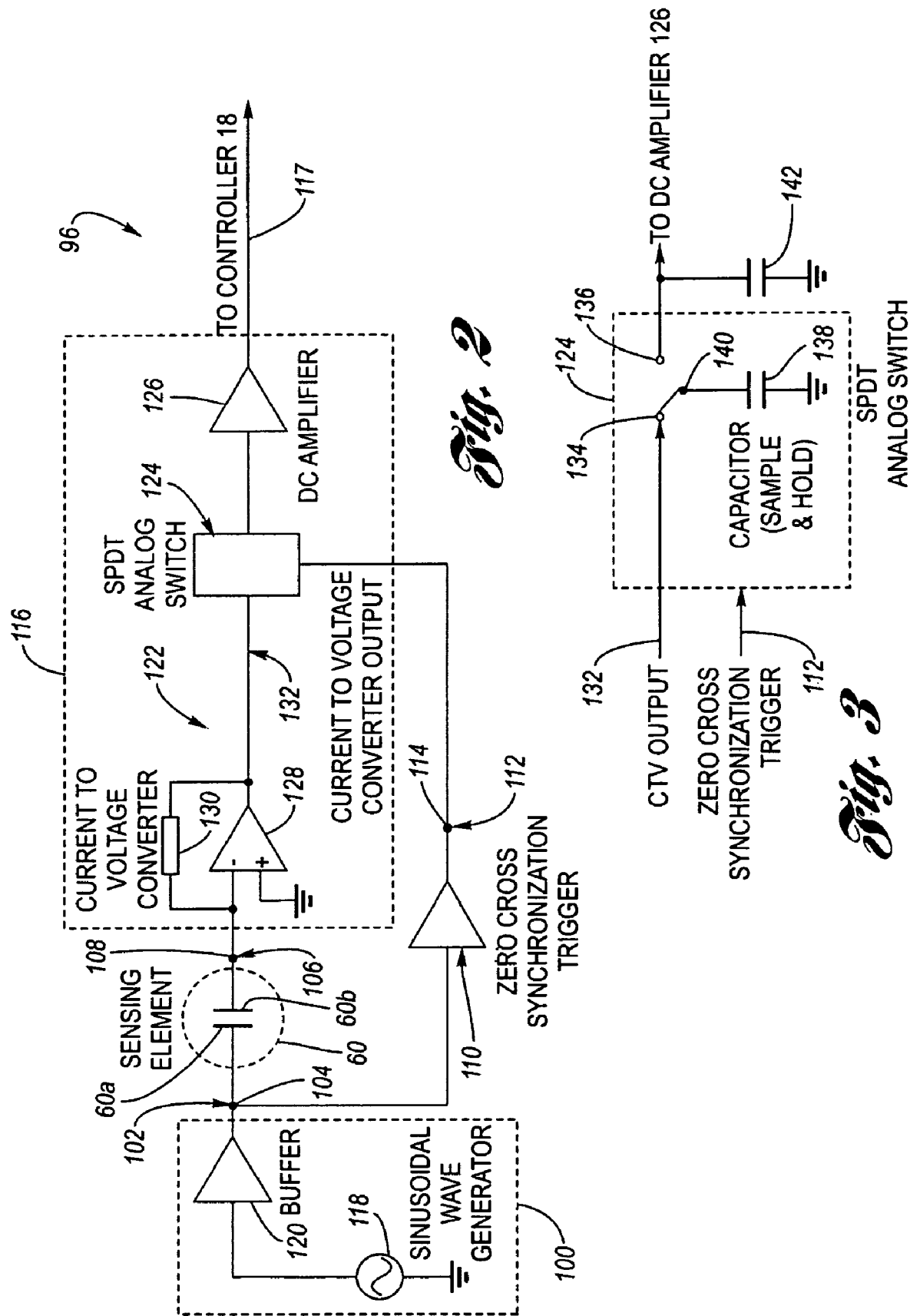

LIQUID PROPERTIES SENSOR CIRCUIT

CROSS-REFERENCE TO RELATED APPLICATIONS

This application claims the benefit of U.S. provisional application Ser. No. 60/890,112 filed Feb. 15, 2007, presently pending, the disclosure of which is hereby incorporated by reference in its entirety.

INCORPORATION BY REFERENCE

This application incorporates by reference in its entirety U.S. application Ser. No. 10/199,651 filed Jul. 19, 2002, now U.S. Pat. No. 6,693,444 B2 entitled "CIRCUIT DESIGN FOR LIQUID PROPERTY SENSOR" issued Feb. 17, 2004 to Lin et al., owned by the common assignee of the present invention.

TECHNICAL FIELD

The invention relates in general to sensors used to detect properties of a fuel, and more particularly, to a sensor for detecting the complex impedance of a fuel.

BACKGROUND OF THE INVENTION

Properties of gasoline, such as its conductivity or dielectric constant, are often important for operation of a motor vehicle. For example, flexible fuel vehicles are known that are designed to run on gasoline as a fuel or a blend of up to 85% ethanol (E85). Such properties can be used to determine the concentration of ethanol in the gasoline/ethanol blend and can also determine the amount of water mixed in with the fuel. For example, experimental data shows that the fuel dielectric constant is directly proportional to the ethanol concentration but relatively insensitive to water contamination, while fuel conductivity is very sensitive to water concentration Thus, for these applications and others, there is a need for a fuel sensor that precisely measures the complex impedance of the fuel.

Current sensor designs have problems handling small capacitance measurements, requiring a relatively large sensing element to increase the signal-to-noise ratio. Further, instead of separately measuring resistance and capacitance, the designs measure total impedance, requiring a relatively high frequency in the 10-100 MHz range to reduce the conductivity impact. Two excitation frequencies are then needed to complete the measurement, a low frequency for resistance measurements and a high frequency for capacitance measurements.

U.S. Pat. No. 6,693,444 entitled CIRCUIT DESIGN FOR LIQUID PROPERTY SENSOR issued to Lin et al. discloses an improvement to the then-prevailing approaches by providing a single frequency circuit design configured to generate magnitude and phase signals corresponding to the complex impedance of the fuel as shown in FIG. 5. Lin et al. disclose a circuit design that characterizes the entire complex impedance of a fuel (i.e., its total complex conductivity). That is, Lin et al. generate both a magnitude signal indicative of total conductivity, including both real (i.e., resistive) and imaginary (i.e., capacitive) parts, as well as a phase signal indicative of the phase angle between an excitation signal and an induced current through the sensing element. While this approach is effective for determining both the dielectric constant as needed for determining ethanol concentration, as well as conductivity as needed for determining water content, further processing is needed to decompose the magnitude signal into its real and imaginary components parts (i.e., one would need to look at just the imaginary part of the magnitude to determine dielectric constant). Additionally, as can be seen in FIG. 5, the circuit is relatively complex.

However, there are certain configurations in the art where just an ethanol concentration sensing system is needed or desired.

SUMMARY OF THE INVENTION

An apparatus in accordance with the present invention provides an improved liquid properties sensor, for example, for determining an ethanol concentration of a gasoline/ethanol blended fuel. The apparatus provides a simplified approach relative to the background art by synchronizing a conductivity current sampling time at the point where the excitation voltage equals zero. When the excitation voltage equals zero, the real component of the total complex conductivity is zero. Accordingly, the total complex conductivity reflects only the imaginary component or part, which as known corresponds to the capacitance of the fuel and thus its dielectric constant. This property can be used to determine ethanol concentration. This synchronization approach obviates the need to decompose the total complex conductivity into its respective real and imaginary parts, and further allows for simplified circuitry (as described herein).

An apparatus in accordance with the invention includes a sensing element in sensing relation with the fuel, a signal generator, a synchronization trigger and a processing circuit. The signal generator is configured to generate an excitation voltage signal of a predetermined frequency. The excitation voltage signal is coupled to the sensing element to thereby produce an induced signal generally indicative of a total complex conductivity of the fuel. The complex conductivity, at various points in time, may generally comprise both real and imaginary component parts.

However, the synchronization trigger is configured to generate a trigger signal responsive to the excitation voltage signal at a time when the real component of the complex conductivity is zero. In a preferred embodiment, this time is when the excitation voltage signal is zero. Therefore, it is at this point in time when the contribution of the real component to the total conductivity is zero, leaving just the imaginary component. The processing circuit is configured to receive the induced signal and produce the output signal in response to the trigger signal, thus synchronizing the sampling of the induced signal with the zero crossing. The output signal thus produced comprises just the imaginary component of the total complex conductivity. The timing of the sampling eliminates the need to provide a circuit for determining a phase angle, resulting in a simpler circuit.

BRIEF DESCRIPTION OF THE DRAWINGS

The present invention will now be described by way of example, with reference to the accompanying drawings:

FIG. 2 is a schematic and block diagram of an apparatus for sensing according to the invention.

FIG. 3 shows, in greater detail, an analog switch portion of FIG. 3.

DETAILED DESCRIPTION OF THE PREFERRED EMBODIMENT

Figure 1:
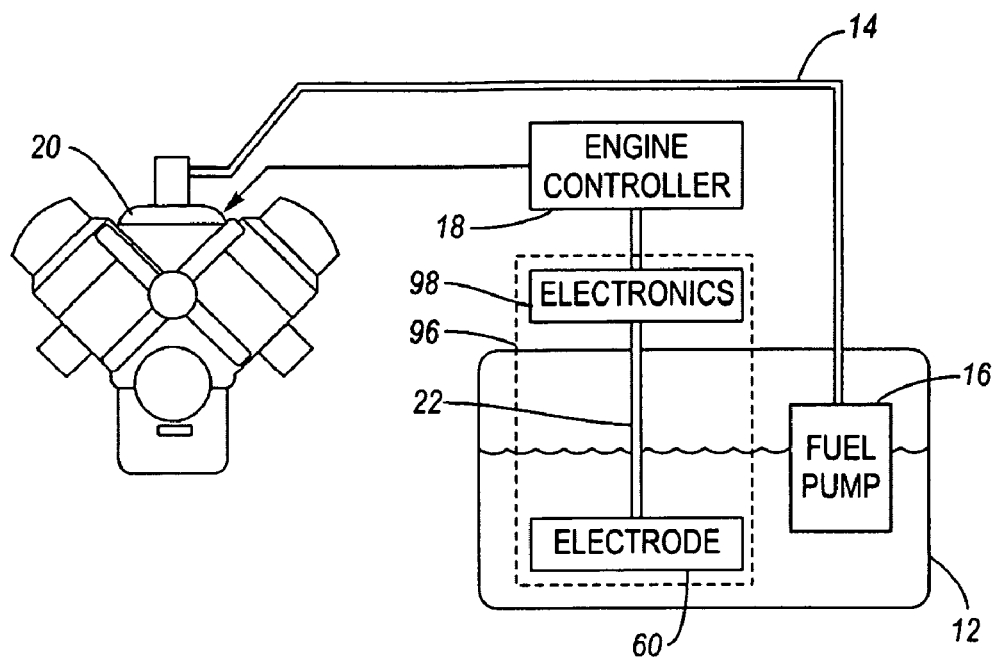
FIG. 1 is a pictorial representation of one placement of the sensor in an automobile.

FIG. 1 shows a sensor apparatus 96, which includes a sensing element 60 and a control circuit or electronics 98, incorporated into an engine control system. Specifically, the sensing element 60 of the sensor apparatus 96 may be located in the fuel tank 12 of a vehicle (not shown) so that it is exposed to fuel. The sensing element 60 is preferably located near the fuel pump 16, which sends fuel to the engine 20 through fuel line 14. However, the sensing element 60 can be located elsewhere where it contacts fuel or is otherwise in sensing relation to the fuel, such as in the fuel line 14. In the illustrated embodiment, the sensing element 60 is submerged in the fuel and excited, and a parameter indicative of a property of the fuel, such as its dielectric constant, is calculated from the induced current measured at a predetermined excitation frequency. It should be understood that in the present disclosure, the sensing element 60, when submerged in the fuel or otherwise in sensing relation with the fuel, appears to the electronics control circuit 98 as a complex load that can be described for simplicity purposes as a parallel combination of a resistor and a capacitor. As described above, the overall, total impedance presented by the sensing element is a complex impedance inasmuch as it is comprised of a real component (resistive) and an imaginary component (capacitive). It should be further understood that impedance and conductivity are interchangeable terms inasmuch as one is the inverse of the other. To determine a property of a fuel, such as its dielectric constant that can be correlated to a concentration of ethanol, the imaginary component is needed. If the impedance (or conductivity) is determined at a time when both real and imaginary components are present, then the quantity will have to be processed (decomposed) to obtain the desired imaginary component. However, in accordance with the invention, if the sampling is synchronized with the zero crossing of the excitation voltage signal, then the real component of the total complex impedance (or conductivity) will be zero. In this case, there is no need for further processing since only the imaginary component will be present.

With continued reference to FIG. 1, in the illustrated embodiment, the control circuit 98 of the sensor apparatus 96 is configured to excite the sensing element 60 through a shielded cable 22, such as a coaxial cable, and receives an induced signal from the sensing element 60. At desired times (e.g., at the time of a zero crossing of the excitation voltage signal), the induced signal is sampled and processed. The control circuit 98 may be configured to include a standard microcontroller, like an engine controller 18 used in automotive applications does, and which includes random access memory (RAM), read-only memory (ROM), input and output means and a processor. The control circuit 98 may be configured to then calculate a capacitance value and supply this value to a diagnostic device or to the engine controller 18. Alternately, the control circuit 98 may provide its output signal (i.e., corresponding to the capacitance and hence to the dielectric constant of the fuel) to the engine controller 18, which itself is configured to perform the desired calculations. In either case, the engine controller 18 can manipulate or otherwise employ the output signal, and the dielectric constant of the fuel that may be derived, to control the amount of fuel the engine 20 receives from the fuel tank 12 through the fuel line 14 relative to the intake of air for the operation of an engine 20.

Figure 4:
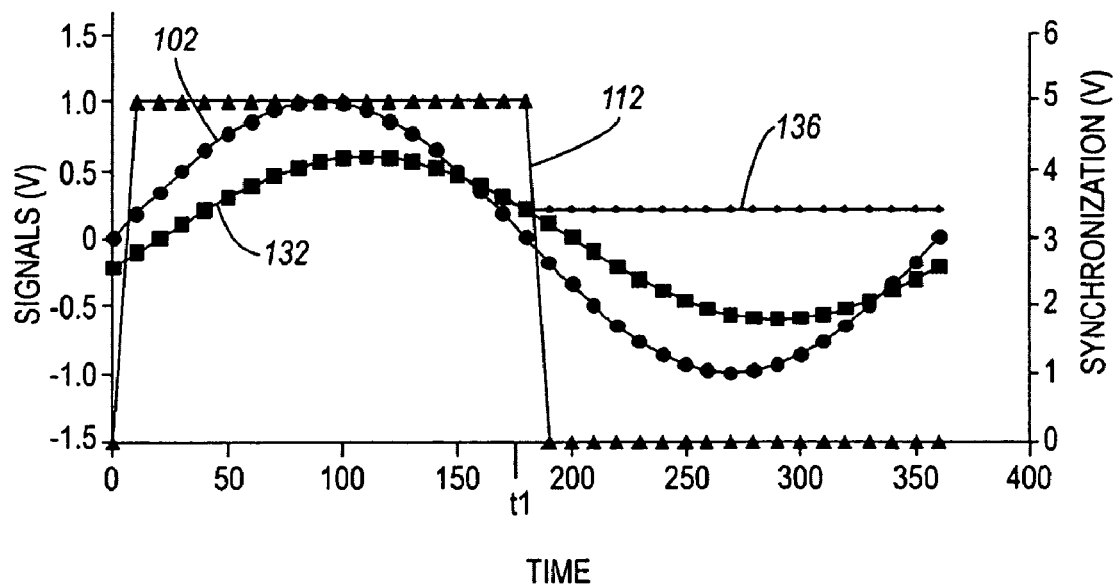
FIG. 4 is a timing diagram showing input, intermediate, and output signals of the inventive apparatus of FIG. 2.

FIGS. 2 through 4 illustrate a preferred embodiment configured to produce an output signal indicative of a property of a fuel, such as its dielectric constant, that may be derived from its measured capacitance. The invention may find particular applicability in flex fuel systems for motor vehicles, where, for example, gasoline/ethanol blends of up to 85% (E85) may be expected.

FIG. 2 is a schematic and block diagram of the apparatus 96. The apparatus 96 includes a signal generator 100 configured to produce an excitation signal 102 on a node 104, a sensing element 60 which will produce an induced signal 106 through a node 108, a synchronization trigger, such as a zero-crossing detector 110, configured to produce a trigger signal 112 on a node 114, and a processing circuit 116 configured to produce an output signal 117 destined for receipt by a main controller 18. The output signal 117 is indicative of a property of a liquid such as its dielectric constant. When the liquid is an ethanol blend fuel, the signal 117 corresponds to a concentration of ethanol in the gasoline/ethanol fuel blend.

With continued reference to FIG. 1, the signal generator 100 is configured to generate the excitation voltage signal 102 at a predetermined frequency. The signal generator 100 includes a sinusoidal source 118 configured to supply a sinusoidal voltage at the predetermined frequency and a buffer 120 having an input coupled to the output of the source 118. The excitation voltage signal 102 is produced at the same frequency as the AC sinusoid voltage input to the buffer 120. The predetermined frequency for the excitation voltage signal 102 is in the range of between about 50 kHz and 1 MHz, and more preferably within the range of between about 200 kHz and 300 kHz. As shown in FIG. 2, the excitation voltage signal 102 is provided to both the sensing element 60 and the zero-crossing detector 110.

The sensing element 60 includes a pair of spaced electrodes 60a and 60b. The electrodes 60a and 60b may comprise electrically-conductive material, such as various metals known in the art for such purpose. Typical embodiments for electrodes 60a and 60b may comprise copper-based alloys (e.g., brass).

The synchronization trigger 110 may comprise a voltage comparator configured as a zero-crossing detector 110, which is coupled to receive the excitation voltage signal 102. The zero-crossing detector 110 is configured to generate the trigger signal 112 when the real component of the induced signal is zero (e.g., zero-crossing of the excitation signal), leaving only the imaginary component. In a preferred embodiment, the zero-crossing detector 110 determines this particular point in time as when the excitation voltage signal 102 is within a predetermined trigger range of zero volts, preferably at zero volts. In a constructed embodiment, the range is preferably a mean value (e.g., zero volts). Thus, the zero-crossing detector 110 is configured to output a HIGH digital signal level when the input AC excitation voltage signal 102 is above such mean, predetermined value. The zero-crossing detector 110 is further configured to output a LOW digital signal level when the excitation voltage signal 102 reaches or goes below the mean value (e.g., of zero volts). As shown in FIG. 4, the trigger signal 112 transitions high-to-low when the excitation signal 102 transitions high-to-low through zero.

The processing circuit 116 receives the induced current signal 106 by way of a connection at the node 108 and is configured to produce the output signal 117 synchronized with the trigger signal 112. The output signal 117 comprises the imaginary component of the total complex conductivity (impedance) observed or measured by the electronics 98 using the sensing element 60. The output signal 117 may be used by the microcontroller 18 to calculate the fuel capacitance in the first instance, and then to determine indirectly the dielectric constant of the fuel, which is indicative of an ethanol concentration of the fuel. It should be understood that in certain embodiments, the ethanol concentration may be determined directly from the measured capacitance or capacitance-related output signal 117, without first calculating an actual dielectric constant value.

The processing circuit 116 includes a current-to-voltage (CTV) converter 122 responsive to the induced current signal 106 for converting the induced current signal 106 into a voltage. The CTV converter 122 includes an operational amplifier 128 and a feedback element 130, having any one of a number of configurations known in the art. In the illustrated embodiment, the non-inverting input terminal of the op amp 128 is connected to ground, while the inverting input terminal is connected to the node 108 to receive the induced current signal 106. Additionally, the inverting input terminal and the output terminal of the op amp 128 are electrically connected by way of the feedback element 130.

The element 130 is formed with a resistor and a capacitor in parallel. The resistor dominates the feedback impedance. The capacitance with very small value is used to reduce feedback noise but not limited phase lag.

Through the foregoing described arrangement, the op amp 128 converts the input current signal into an induced voltage signal 132. The induced voltage signal 132 is a sinusoid voltage with a phase angle identical to the induced sinusoidal current going through the sensing element 60. It should be understood that at the time when the input excitation voltage signal 102 is zero, the real component of the induced current through the sensing element 60 is also equal to zero. Accordingly, the CTV 122 output signal 132 reflects only the imaginary component of the induced current, now voltage, signal.

The processing circuit 116 further includes an analog switch circuit, such as a single-port-double-throw (SPDT) analog switch 124, which will be described immediately below in greater detail. The processing circuit 116 further includes an output DC amplifier 126, which is configured to amplify the output of the analog switch 124 to produce the output signal 117. The DC amplifier 126 has a low input bias current.

FIG. 3 shows analog switch 124 in greater detail. The switch 124 has an input terminal 134, an output terminal 136 and a sample-and-hold arrangement, such as a capacitor 138 connected to a common node 140. The switch 124 is controlled by the trigger signal 112 in a manner to be described. In a constructed embodiment, when the trigger signal 112 is HIGH, the switch 124 is in a first state, in which the common node 140 is connected to the input terminal 134 to thereby track the changes in the induced voltage signal 132. Accordingly, the sample-and-hold capacitor 138 is charged with and thus tracks the CTV output signal 132. The switch 124 further includes a second state. When the trigger signal 112 goes LOW due to a zero-crossing detection by detector 110, the trigger signal 112 is operative to control the switch 124 into the second state. In the second state, the common node 140 is switched from the input terminal 134 to the output terminal 136, and the capacitor 142 is charged with the tracked voltage which is in turn electrically-connected to the DC amplifier 126. Due to the low input bias current of the DC amplifier 126, the charge on the capacitor 142 can maintain a relatively constant voltage, which establishes the sampled induced voltage signal 132 on the output terminal 136. It is preferred that the sample and hold capacitor 138 has larger capacitance value than the capacitor 142. The voltage on the output terminal 136 is substantially identical to the CTV output signal 132 instantaneously after the zero crossing event. The DC amplifier 126 amplifies this output, which is directly proportional to the imaginary component of the sinusoidal current going through the sensing element 60.

It should be appreciated that the sample-and-hold capacitor 138 develops a DC voltage output signal after the zero-crossing event, and thus no rectifiers, filters and the like are necessary, as may have been the case in the prior art where the magnitude signal constituted a sinusoidal signal. This sampling approach provides for a simplified circuit design.

FIG. 4 is a timing diagram illustrating the operation of the present invention. As can be seen, when the excitation voltage signal 102 crosses zero volts at near time $t_1$, the trigger signal 112 transition from a logic HIGH state to a logic LOW state. Between time zero and time $t_1$, the output of the sample and hold capacitor 138 at node 140 is coupled to and thus tracks the changes of the CTV output signal 132 (i.e., the two traces overlay each other). However, at time $t_1$, the trigger signal 112 controls the switch 124 to disconnect the common node 140 from the CTV output signal 132. At the point of disconnection, the voltage on the output terminal 136 "holds" its level as it existed at the time the trigger signal 112 transitioned HIGH-to-LOW. As described above, since the time where the excitation voltage signal 102 is at zero volts is where the real (resistive) component of the total complex conductivity (impedance) is also zero, the CTV output signal 132 at that time reflects only the imaginary capacitive component. This signal is transferred to the output terminal 136 and is subsequently amplified by the DC amplifier 126.

In sum, the present invention overcomes some of the complexity issues associated with prior approaches. The imaginary component of the total complex conductivity is that which corresponds to the capacitive part of the complex load formed by the fuel and the sensing element. In prior approaches, the imaginary conductivity could be calculated using equation (1) below when total conductivity and the phase angle are known; however, this decomposition was somewhat complex.

$$I_m(\text{conductivity}) = \sin(\text{phase\_angle}) * \text{total\_conductivity} \quad (1)$$

where the phase_angle is the calculated or measured phase angle and the total_conductivity is the determined magnitude.

However, the present invention improves upon prior approaches when only the imaginary part is desired. In particular, the present invention provides for synchronizing the conductivity current sampling time at the point where the excitation voltage equals to zero. At this time, the contribution of the real part (resistive) to the total conductivity is zero, leaving just the imaginary part, which can be measured directly without the need for complex decomposition processing. This results in a greatly simplified system and method for determining a property of a liquid, as explained above.

Figure 5:
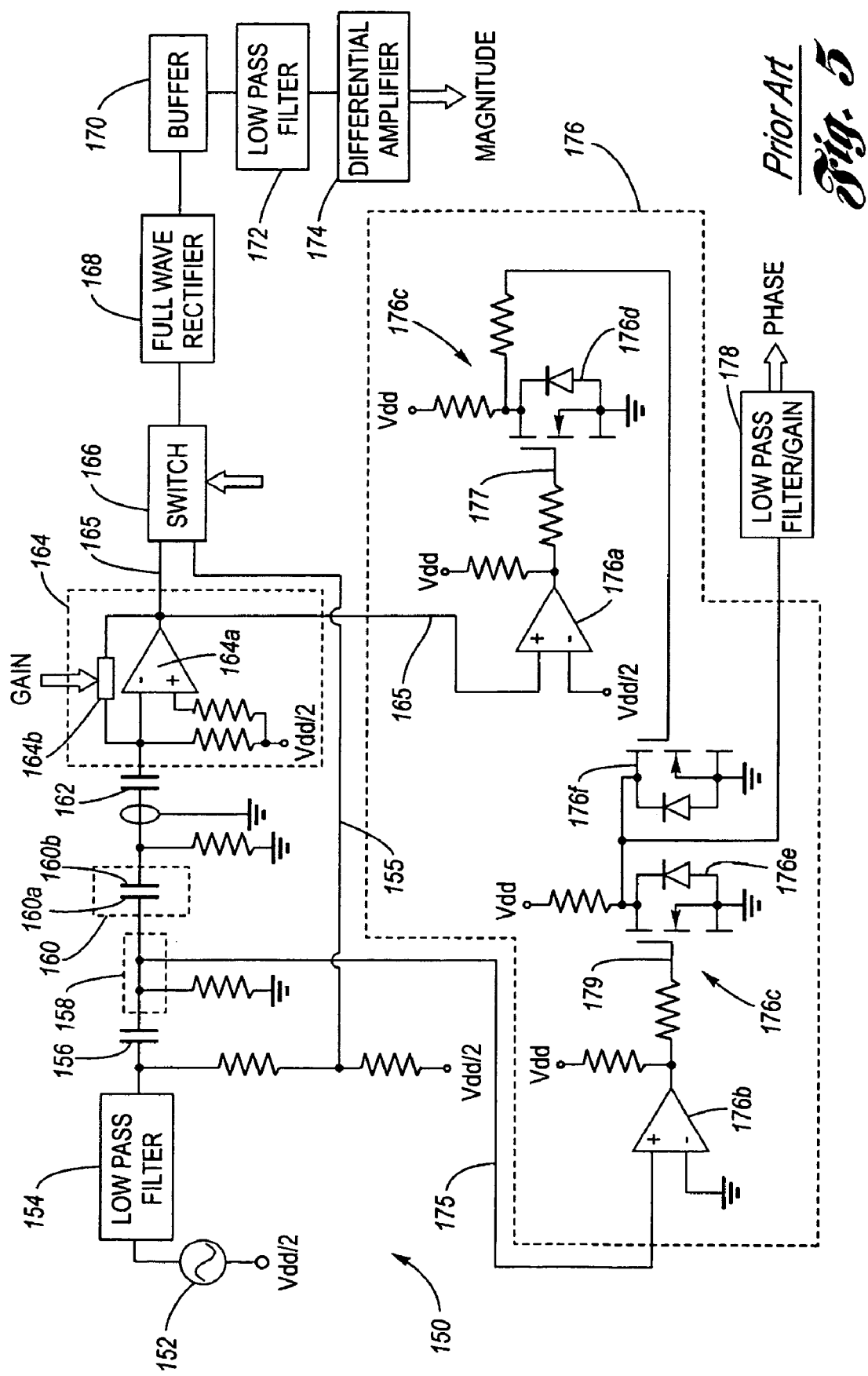
FIG. 5 is a schematic and block diagram of a known circuit design for a sensing system.

FIG. 5 shows the known circuit design for a liquid property sensor, as described in the Background, and as disclosed in U.S. Pat. No. 6,693,444 issued to Lin et al. entitled CIRCUIT DESIGN FOR LIQUID PROPERTY SENSOR. This circuit develops both a magnitude signal indicative of total conductivity as well as a phase signal indicative of the phase angle between the excitation signal and the current through the sensing element. For completeness, a description of this circuit will be given below.

As described in the Background, it is know to provide a complex impedance circuit that is based on a single excitation frequency. This apparatus provides both a magnitude and phase angle. In this regard, FIG. 5 is a block diagram of a sensor apparatus 150 that can perform this impedance determination. The sensing element 160 of the sensor 150 comprises two spaced electrodes, an excitation plate 160a and a sensing plate 160b, both made of a conductive material. The sensing element 160 is submerged in the fuel and excited by a sinusoidal wave generator 152. The sinusoidal wave generator 152 generates a sinusoidal voltage centered at the voltage Vdd/2. By example, the peak-to-peak amplitude is around 4 volts. The sinusoidal voltage is at a single frequency in the range of 10 kHz to 100 kHz. If the generator is a single stage sine wave generator 152, the voltage is first filtered through a standard low pass filter 154 to filter out high order harmonics. Alternatively, of course, a dual stage sine wave generator 152 can be used and the low pass filter 154 omitted.

The filtered voltage feeds through a voltage divider tied to Vdd/2. The resulting voltage signal provides a temperature reference voltage 155 to a switch 166 The temperature reference voltage 155, and its use with the switch 166, is discussed further herein. The filtered voltage also provides an excitation signal to the sensing element 160 through the shielded cable 122 at node 158. Specifically, the filtered voltage flows through a DC block capacitor 156, and the resulting excitation signal reaches the excitation plate, or electrode, 160a of the sensing element 160. Node 158 brings the DC voltage of the excitation plate 160a of the sensing element 160 down to ground through a grounding resistor.

The control circuit 148 receives the excitation signal from node 158 and supplies it as a reference input excitation signal 175 for a pulse width modulated (PWM) generator 176, discussed herein.

The control circuit 148 receives the current induced on the sensing element 160 from the sensing electrode 160b through the shielded cable 122. Preferably, the sensing plate, or electrode, 160b of the sensing element 160 is grounded through a resistor to bring the DC components of this induced signal to ground. Together with the ground provided for the excitation plate 160a at node 158, this ground assures that the signals supplied to the remainder of the control circuit 148 have no DC components. Also, and as shown in FIG. 5, the shield or the shielded cable 122 is preferably brought to ground, optionally through a resistor (not shown). As additional protection against DC components in the induced signal, a series-connected DC blocking capacitor 162 filters the induced signal prior to it being supplied to the inverting input of an operational amplifier (op amp) 164a configured as a current-to-voltage converter 164.

In the current-to-voltage converter 164, the inverting input of the op amp 164a is raised to Vdd/2 through a resistor, as is the non-inverting input of the op amp 164a. Feedback is supplied through a feedback impedance 164b, wherein either the reactive component or the resistive component of the feedback impedance 164b is minimized. Preferably, the feedback impedance 164b provides the op amp 164a with a variable gain such that the resolution of the output signal MAGNITUDE is adjustable by changing the feedback impedance. Ideally, the output of the converter 164 is a sinusoidal voltage centered at, for example, 2.5 volts. Depending upon the characteristics of the fuel, however, the op amp 164a can saturate, and the resolution of the signal MAGNITUDE, discussed herein, diminishes. One characteristic affecting the resolution of the signal is the ethanol content.

In the preferred embodiment, the feedback impedance 164b comprises a plurality of parallel complex impedances enabled by a gain control signal GAIN. By example, four complex impedances are connected to four outputs of a digital switch, and each complex impedance includes a large resistance value in parallel with a small capacitance value. The gain control signal GAIN is a digital signal generated by the engine controller 118 or a microcontroller (not shown) of the control electronics 148, here [0:0] to [1:1]. Whichever controller receives the output MAGNITUDE sends the signal GAIN to the digital switch, adjusting the gain of the op amp 164a until the output MAGNITUDE reaches the desired resolution. Where the fuel has a large capacitance, a small gain is desirable; where the fuel has a small capacitance, a large gain is desirable.

The output of the current-to-voltage converter 164 is a sinusoidal voltage signal 165 centered at, for example, 2.5 volts, and representative of the complex impedance of the fuel. The sinusoidal voltage signal 165, like the temperature reference voltage 155, is preferably fed into the switch 166. The switch 166 can be an analog switch, such as ADG419 from Analog Devices, Inc. of Norwood, Mass., which receives a sampling signal SELECT from the engine controller 118 or a microcontroller (not shown) of the control electronics 148. The sampling signal SELECT determines which of the sinusoidal voltage signal 165 and the temperature reference voltage 155 are used to calculate the output signal MAGNITUDE. This provides a means of correcting the output signal MAGNITUDE for temperature variations of the circuit board on which the control electronics 148 are mounted.

More specifically, the temperatures to which the sensor 150 is exposed vary significantly with operation of the vehicle in which the sensor 150 is installed. Circuit board temperatures can range, for example, from −40° C. to 125° C. Normally, the sampling signal SELECT is such that the sinusoidal voltage signal 165 passes through and is used to determine the output signal MAGNITUDE. The output signal MAGNITUDE is a DC voltage used by the controller in a lookup table, for example, to determine the impedance magnitude of the complex impedance. Testing shows, however, that signal drops for a nominal magnitude of 2 volts can be 10% or more as the temperature increases. The present invention addresses this problem by, at specific predetermined intervals, sending a sampling signal SELECT that enables the switch 166 to pass the temperature reference voltage 155 on to the remainder of the control electronics 148 that determines the output signal MAGNITUDE. This output signal MAGNITUDE is compared to the expected magnitude based upon the value of the voltage reference Vdd/2. A ratio, or adjustment factor, of the output signal MAGNITUDE developed from the temperature reference voltage 155 to the expected voltage is used to adjust the output signal MAGNITUDE based upon the sensed sinusoidal voltage signal 165. In this manner, the output signal MAGNITUDE is adjusted for temperature variation prior to using it to determine the impedance magnitude of the complex impedance.

FIG. 5 shows one circuit design that can detect the peak of the sinusoidal voltage output of the switch 166, whether it is the sensed sinusoidal voltage signal 165 or the temperature reference voltage 155. First, the signal is rectified by a standard full wave rectifier 168. After passing through a buffer 170, the signal is filtered through a low pass filter 172 to remove its AC components. The resulting DC signal is then fed through a differential amplifier 174, which sends the amplified DC signal, output signal MAGNITUDE, to a microcontroller, such as the engine controller 118. The engine controller 118 then adjusts the output signal MAGNITUDE by the last calculated adjustment factor if the output signal MAGNITUDE is based upon the sensed sinusoidal voltage signal 165, or a new adjustment factor is determined if the output signal MAGNITUDE is based upon the temperature reference voltage 155.

Optionally, the actual magnitude of the complex impedance can be determined from this voltage output signal MAGNITUDE. To do this, the engine controller 118 compares the output signal MAGNITUDE to values on a look up table determined in prior calibration experiments wherein the look up table correlates voltage outputs to impedance magnitudes. Alternately, a mathematical relationship between these two variables can be developed and used by the engine controller 118 to determine the impedance magnitude from the output signal MAGNITUDE.

The output of the current-to-voltage converter 164, which is representative of the complex impedance of the fuel, takes two paths. As described above, the sinusoidal voltage signal 165 is supplied to a peak detector, or any kind of an AC amplitude to DC converter that detects the magnitude of the peak of the signal. Second, the sinusoidal voltage signal 165 is supplied to the PWM generator 176, which compares that voltage signal 165 to the reference input excitation signal 175 to determine the phase of the complex impedance. A multitude of circuits can determine this phase from the two input signals; one is shown in FIG. 5.

The PWM generator 176 of FIG. 5 includes two comparators 176a and 176b and a pulse-width modulator circuit 176c. In the example, the sinusoidal voltage signal 165 is a sinusoidal voltage centered at 2.5 volts. It is supplied to the non-inverting input of the comparator 176a, while the inverting input of the comparator 176a is at Vdd/2. The output of the comparator 176a is a square wave 177 from 0 to 5 volts with a frequency corresponding to that of the sinusoidal voltage signal 165. The reference input excitation signal 175 is a sinusoidal voltage centered at 0 volts at the same frequency as the sinusoidal voltage signal 165. However, the sinusoidal voltage signal 165 is offset in phase from the reference input excitation signal 175, where the offset corresponds to the phase of the impedance between the node 158 and the output of the op amp 164a of the current-to-voltage converter 164. The reference input excitation signal 175, like the sinusoidal voltage signal 165, is similarly supplied to the non-inverting input of a comparator 176b, while the inverting input of the comparator 176b is at ground. The output of the comparator 176b is a square wave 179 from 0 to 5 volts with a frequency corresponding to that the reference input excitation signal 175 and with the same phase offset from the sinusoidal voltage signal 165. The two square waves 177 and 179 are provided to two field-effect transistors (FET) of a pulse-width modulator circuit 176 comprising three FETs. More specifically, each of the two square waves 177, 179 is provided as an input to the gate of a corresponding FET 176d, 176e. The source of each of the three FETs 176d-f is grounded, while the drain of each of the three FETs 176d-f is raised to Vdd through a resistive load. The output voltage at the drain of the FET 176d receiving the square wave 177 is the input voltage signal for the gate of the third FET 176f, while the output voltage of the drain of the FET 176e receiving the square wave 179 is tied to the output voltage of the drain of the third FET 176f. Thus, the output of the pulse-width modulator circuit 176c, and of the PWM generator 176, is a square wave from 0 to 5 volts with a duty cycle based upon the difference in phase, or the phase offset, of the square wave 177, representing the induced signal, and the square wave 179, representing the excitation signal.

The output of the PWM generator 176 is passed through a conventional low pass filter with a fixed gain 178. The resulting output signal PHASE is a square wave with a duty cycle ranging from 0%-50%, which is provided to the same controller as the output signal MAGNITUDE, such as the engine controller 118. The controller 118 calculates the duty cycle according to conventional methods. Through prior calibration, another look up table can be provided in the engine controller 118 whereby a duty cycle of 0%-50% corresponds to a phase of the complex impedance of 0°-180°. Once the controller 118 has the duty cycle of the output signal PHASE,
it can use the look up table to determine the phase of the complex impedance. Of course, as with the calculation of the magnitude of the complex impedance, a mathematical relationship governing the relationship of the output signal PHASE to the phase of the complex impedance can be developed from the prior calibration experiments and used instead of the look up table. Given the complex output comprising the magnitude and the phase outputs, the microcontroller or engine controller 118 can determine the resistance and capacitance of the fuel by a simple calculation.

Thus is presented in FIG. 5 a sensor design can measure capacitance down to the picofarad range and measure magnitude and phase difference using a single excitation frequency in the range of 10-100 kHz. A simple calculation gives the precise measurements of resistance and capacitance.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. An apparatus for generating an output signal indicative of a property of a fuel, said apparatus comprising:
   a sensing element in sensing relation with the fuel;
   a signal generator configured to generate an excitation voltage signal of a predetermined frequency, said excitation voltage signal being coupled to said sensing element to thereby produce an induced signal indicative of a complex conductivity of the fuel having imaginary and real components;
   a synchronization trigger configured to generate a trigger signal responsive to said excitation voltage signal at a time when a said real component is zero; and
   a processing circuit configured to receive said induced signal and sample said induced signal in response to said trigger signal, said processing circuit being further configured to produce said output signal based on said sample induced signal, said output signal comprising said imaginary component of said complex conductivity and corresponding to a property of the fuel.

2. The apparatus of claim 1 further comprising means for calculating a capacitance presented by said sensing element using said output signal.

3. The apparatus of claim 2 wherein said calculating means comprises a microcontroller configured to receive said output signal.

4. The apparatus of claim 2 wherein said sensing element comprises two spaced electrodes of a predetermined configuration, said calculating means being configured to determine a dielectric constant of the fuel using the capacitance and the predetermined configuration of the sensing element.

5. The apparatus of claim 1 wherein said sensing element comprises two spaced electrodes.

6. The apparatus of claim 1 wherein said signal generator comprises a sinusoidal source supplying a sinusoidal voltage at said predetermined frequency to said sensing element.

7. The apparatus of claim 5 wherein said predetermined frequency is in a range of 50 kHz to 1 MHz.

8. The apparatus of claim 7 wherein said range extends between 200 kHz and 300 kHz.

9. The apparatus of claim 1 wherein said induced signal through said sensing element comprises an induced current signal, said processing circuit including a current-to-voltage converter responsive to said induced current signal configured to generate an induced voltage signal; and an analog switch having an input terminal, an output terminal and a sample-and-hold arrangement with a common node, said input terminal being configured to receive said induced voltage signal, said switch having a first state in which said common node is connected to said input terminal to track changes in said induced voltage signal, said switch having a second state where said common node is switched from said input terminal to said output terminal in response to said trigger signal, thereby establishing a sampled induced voltage signal on said output terminal.

10. The apparatus of claim 9 wherein said sample-and-hold arrangement is configured to maintain said sampled induced voltage signal on said output terminal.

11. The apparatus of claim 9 wherein said current-to-voltage converter comprises an operational amplifier with an adjustable gain.

12. The apparatus of claim 9 wherein said processing circuit further includes a DC output amplifier coupled to said output terminal of said analog switch and configured to generate said output signal, said output signal being proportional to said imaginary component.

13. The apparatus of claim 1 wherein said synchronization trigger comprises a zero-crossing detector configured to generate said trigger signal.

14. The apparatus of claim 13 wherein said detector is configured to generate said trigger signal when said excitation voltage signal transitions from a positive voltage to a negative voltage.

* * * * *